(12) United States Patent
Zhang

(10) Patent No.: US 11,058,529 B2
(45) Date of Patent: Jul. 13, 2021

(54) COMPOSITE SOFT TISSUE REPAIR MATERIAL STABLE IN REPAIR AREA

(71) Applicants: Shanghai Zhuoruan Medical Technologies Co., Ltd, Shanghai (CN); Zhuoruan Medical Technologies (Suzhou) Co., Ltd, Jiangsu (CN)

(72) Inventor: Jian Zhang, Shanghai (CN)

(73) Assignees: Shanghai Zhuoruan Medical Technologies Co., Ltd, Shanghai (CN); Zhuoruan Medical Technologies (Suzhou) Co., Ltd, Taicang (CN)

( * ) Notice: Subject to any disclaimer, the term of this patent is extended or adjusted under 35 U.S.C. 154(b) by 78 days.

(21) Appl. No.: 16/117,772

(22) Filed: Aug. 30, 2018

(65) Prior Publication Data

US 2018/0360585 A1   Dec. 20, 2018

Related U.S. Application Data

(63) Continuation-in-part of application No. PCT/CN2017/073395, filed on Feb. 13, 2017.

(30) Foreign Application Priority Data

Mar. 1, 2016  (CN) .......................... 201610115203.4

(51) Int. Cl.
*A61F 2/00*    (2006.01)
*A61L 27/44*   (2006.01)
(Continued)

(52) U.S. Cl.
CPC ............ *A61F 2/0063* (2013.01); *A61L 27/16* (2013.01); *A61L 27/3629* (2013.01);
(Continued)

(58) Field of Classification Search
None
See application file for complete search history.

(56) References Cited

U.S. PATENT DOCUMENTS

| | | | |
|---|---|---|---|
| 6,638,312 B2* | 10/2003 | Plouhar | A61F 2/0063 623/23.72 |
| 2011/0152196 A1* | 6/2011 | Shah | A61L 27/3633 514/17.2 |
| 2015/0209478 A1* | 7/2015 | Matheny | A61L 27/14 424/426 |

FOREIGN PATENT DOCUMENTS

| | | |
|---|---|---|
| CN | 201664349 U | 12/2010 |
| CN | 102698318 A | 10/2012 |
| CN | 104822342 A | 8/2015 |

OTHER PUBLICATIONS

Melman, L; et al; "Early biocompatibility of crosslinked and non-crosslinked biologic meshes in a porcine model of ventral hernia repair" Hernia, 15, 157-164, 2011 (Year: 2011).*

(Continued)

*Primary Examiner* — David W Berke-Schlessel
(74) *Attorney, Agent, or Firm* — Maier & Maier, PLLC

(57) ABSTRACT

A composite soft tissue repair material stable in repair area, includes a middle mechanical reinforcement layer containing crosslinked acellular matrix; and upper and lower layers containing non-crosslinked acellular matrix, wherein the upper and lower layers completely encapsulate the middle mechanical reinforcement layer to form a sandwich structure. The present invention combines the advantages of crosslinked acellular matrix and non-crosslinked acellular matrix, including high histocompatibility, no viscera erosion, uniform thickness of the whole material, resistance to infection, long-term mechanical stability of the repair area, et al, which has good application prospects.

8 Claims, 4 Drawing Sheets

(51) Int. Cl.
*A61L 27/36* (2006.01)
*A61L 27/50* (2006.01)
*A61L 27/16* (2006.01)

(52) U.S. Cl.
CPC ........... *A61L 27/3633* (2013.01); *A61L 27/44* (2013.01); *A61L 27/50* (2013.01); *A61L 2430/34* (2013.01)

(56) References Cited

OTHER PUBLICATIONS

Gilber, Thomas W; et al; "Morphologic Assessment of Extracellular Matrix Scaffolds for Patch Tracheoplasty in a Canine Model" Annals of Thoracic Surgery, 86, 967-974, 2008 (Year: 2008).*
Foreword of Standard: GB/T528-2009: "Rubber, vulcanized or thermoplastic—Determination of tensile stress-strain properties" *National Standard of the People's Republic of China*, issued on Apr. 24, 2009, pp. 1-4 of 33.

* cited by examiner

COMPOSITE SOFT TISSUE REPAIR MATERIAL STABLE IN REPAIR AREA

CROSS REFERENCE TO RELATED APPLICATIONS

This application is a continuation in part application of PCT/CN2017/073395, which was filed on Feb. 13, 2017, and which claims priority to CN 201610115203.4, which was filed on Mar. 1, 2016, and which is herein incorporated by reference.

TECHNICAL FIELD

The present invention relates to the field of soft tissue repair, and particularly to a composite soft tissue repair material stable in repair area.

BACKGROUND OF THE INVENTION

Large tissue defects repair represented by abdominal wall defects is a difficult problem in surgery. Acellular matrix biologic patches composed of allogeneic or xenogeneic extracellular matrix are common choices in clinical applications.

However, the long-term efficacy of the acellular matrix biologic patches is still controversial, mainly because the repair areas of some cases experience loss of laxity, Eventration (Bulge), or even hernia recurrence, especially when complicated and large abdominal wall defect is repaired using the non-crosslinked biologic patches by bridging method. Some studies have found that more than 50% of the cases with abdominal wall bulging in repair area one year after surgery, and severe cases are therefore surgically implanted with synthetic patches to reinforce the repair area. As for the existing precautions, only some manufacturers suggest that in use of the biologic patches such as an acellular dermal patch, the patch should be stretched as much as 50% of the original area after the material is hydrated, and then used for defect repair, because the incidence of long-term abdominal wall bulging will increase without stretching. A long-term research has found that the long-term loss of laxity in repair area of the biologic patches is due to the simultaneous biodegradation accompanying with remodeling (endogenous biological healing). If degradation of the implant material does not balance with the new tissue remodeling, the tension from the abdominal cavity will not be supported or transmitted entirely and timely, resulting in loss of laxity, bulging or hernia recurrence in the repair area of the biological patches.

In order to allow the implanted patches-new tissue undergo a smooth transfer of tissue tension, the researchers have considered two methods:

1. crosslinking delayed the degradation of acellular matrix or turned it into non-degradable acellular matrix: the triple helical scaffold structure of collagen was bonded to slow down the effects of collagenase, and improve the strength and durability of implantations. The disadvantages of the crosslinking are obvious, crosslinking changes remodable acellular matrix material into leather with chronic foreign body reaction, leading to the formation of fibrous encapsulation far more than remodeling of the biologic scaffold during the process of soft tissue repair.

One of the focus of biomaterial research is how to improve the crosslinking process. During the crosslinking process of collagen, changes of the structure in natural tissue should be avoided to optimize the scaffold remodeling, thus maximizing cell infiltration and vascularization, fastest and most abundant extracellular matrix loading, minimizing or no inflammatory response and no fibrous encapsulation.

2. Non-degradable components or slowly degradable components were introduced into the non-crosslinked biologic patches. CN201664349U discloses a novel composite hernia and body wall repair patch. The patch is manufactured by utilizing medical adhesive to adhere polymer mesh to biologic material. The composite hernia repair patch can effectively isolate the direct contact between the abdominal organs and the synthetic mesh. The lightweight mesh can play the role of "steel bar" in the repair area in the long term, optimize the overall tensile performance of the composite mesh, significantly reduce the recurrence of hernia, and improve the hand feeling.

CN102698318A discloses a biomaterial composite patch. The patch is composed of synthetic material as base layer, and extracellular matrix/decellularized tissue matrix material biological patch, or bio-synthetic material patch or other synthetic degradable material as a supplemental layer. The base layer and the supplemental layer are assembled by medical suture or medical glue or other methods. The basic mechanism and structure of the patch are the same as that of CN201664349U. The patches have the following problems.

(1) The polymer mesh covers the surface of the acellular matrix and directly contacts with host tissues after implantation, changing the immune response type in the host-material margin of the acellular matrix (M2-type macrophage infiltration in dominance→M1-type macrophage infiltration in dominance).

(2) Most biological materials are applied to the contaminated wounds, and the bacteria are easy to adhere to polymer material. Therefore, after the bacterial adhesion, biofilms can be formed that protect the bacteria from host immune defense and antibiotics, so that the bacteria can grow and proliferate locally for a long time and cause chronic infection of wounds.

(3) The polymer materials have problems such as chronic viscera erosion and shrinkage of repair areas.

Besides, there are also applications composed of non-degradable components and acellular matrix, in which non-degradable components are placed between multi-layered acellular matrix. American Food and Drug Administration has approved the application of a composite hernia repair patch Zenapro® (COOK Biotech, USA), namely, hybrid hernia device. Zenapro is a product composed of porcine small intestinal submucosa as an outer layer and a polypropylene mesh sheet as an inner layer (FIG. 1), which is applied in abdominal hernia repair by bridging method to reinforce the tensile strength of repaired abdominal wall. Further, the product combining synthetic material and acellular matrix material has problems that:

(1) The material is thick, and thus is not conducive to operation, the thickness of woven nods of the synthetic mesh in the materials can be as thick as 2 mm or more. For example, in laparoscopic operation, the patch is required to be rolled and to pass through a puncture cannula of 10 mm or 12 mm in diameter, but a thick patch cannot be rolled to get through;

(2) The polymer fiber inside the material and the acellular matrix cannot be completely composite to form a flat whole, and the surface has a poor flatness, and includes dead space (as shown in FIG. 1), which is a good colonization space for bacteria and can easily lead to infection. Bacterial biofilm can easily form in the dead space, which requires reoperation to take out the patch for the infection cannot be cleared by even if the dosage of antibiotics increased by 1000 times.

(3) The steel bar or the supporting structure of the above materials are all synthetic materials, under the circumstances of fast degradation or unsatisfied regeneration of surface acellular matrix, which is due to implantation site, surgical operation, progress of disease (such as effusion in repair area leads to shortened degradation), synthetic material cannot be well encapsulated and exposed to viscera, and thus cause viscera erosion and re-operation is required.

Therefore, an ideal patch of composite structure should have the characteristics of maintaining long-term mechanical stability, high histocompatibility, no viscera erosion, high integrity, and low thickness for convenient operation.

SUMMARY OF THE INVENTION

The technical issue the present invention aims to solve is to provide a composite soft tissue repair material stable in repair area, which combines the advantages of crosslinked materials and non-crosslinked materials, including high histocompatibility, no viscera erosion, resistance to infection, mechanical stability of the repair area or the like, and thus has good application prospects.

A composite soft tissue repair material stable in repair area of the present invention includes a middle mechanical reinforcement layer containing crosslinked acellular matrix; and upper and lower layers containing non-crosslinked acellular matrix, wherein the upper and lower layers completely encapsulate the middle mechanical reinforcement layer to form a sandwich structure.

The crosslinked acellular matrix is encapsulated by the non-crosslinked acellular matrix, rather than apply to the surface of the non-crosslinked acellular matrix. The non-crosslinked acellular matrix isolates the direct contact with the crosslinked acellular matrix with the host tissue after implantation, does not change the immune response type in host-material margin of the composite material as a whole, and avoids colonization of the bacteria to non-absorbable components.

The edge of the middle mechanical reinforcement layer is 2 mm to 15 mm away from those of upper and lower layers. This ensures that no mechanical reinforcement layer is exposed to the surface of the composite material. The non-crosslinked acellular matrix acts as surface layers to endow the composite material with high histocompatibility and capability to direct contact with the organs. The tensile strength for the middle mechanical reinforcement layer is >8 N/cm (the natural human abdominal fascia strength), and an elasticity thereof is slightly lower than the natural human abdominal fascia strength, and the middle mechanical reinforcement layer is mechanically stable in a long term.

The mass ratio of crosslinked acellular matrix in the middle mechanical reinforcement layer to the non-crosslinked materials acellular matrix in the upper and lower layers is 1:20 to 1:0.1, so as to ensure that non-degradable components of relatively low contents can compensate for the instability of the repair area caused by unsatisfied tissue regeneration induced by the non-crosslinked acellular matrix in special cases.

The crosslinked acellular matrix is derived from submucosa of hollow organs, dermis, pericardium, peritoneum, pleura, basement membrane, or amniotic membrane of human or mammalian; with crosslinking degree from 1% to 100%. The crosslinking degree is variable, but the long-term stable mechanical properties thereof should meet the requirements of the middle mechanical reinforcement layer.

The non-crosslinked acellular matrix is derived from submucosa of hollow organs, dermis, pericardium, peritoneum, pleura, basement membrane, or amniotic membrane of human or mammalian.

The crosslinked acellular matrix contains one or more sources of crosslinked acellular matrix derived from different sources.

The non-crosslinked acellular matrix contains one or more non-crosslinked acellular matrix derived from different sources.

The crosslinked acellular matrix or the non-crosslinked acellular matrix may be single-layered or multi-layered structures, and the numbers of layers should be changed depending on the position of use.

In order to composite the crosslinked and non-crosslinked acellular matrix into a whole and avoid delamination, the crosslinked acellular matrix may be laminated, selectively combined with non-crosslinked acellular matrix, into a whole layer through a woven pattern, or interlacing pattern, or perforated or strip-like crosslinked acellular matrix placed between the non-crosslinked acellular matrix, facilitating formation of chemical bonds between layers or sheets through physical methods.

The middle mechanical reinforcement layer and the upper and lower layers of non-crosslinked acellular matrix are laminated into a whole by one or more of medical adhesive, tying with suture, vacuum pressing and heat pressing. In the case of physical methods, such as vacuum pressing or heat pressing, chemical bonds are formed between layers and sheets of acellular matrix.

Preferably, the medical adhesive and the suture are composed of absorbable components. The vacuum pressure of the vacuum pressing is −100 mmHg to −760 mmHg, and the acting duration is 0.5 h to 72 h.

The composite soft tissue repair material is further perforated penetrating the material, wherein the perforations have a diameter of 1 mm to 5 mm, and the spacing between perforations is 1 mm to 50 mm, and no crosslinked acellular matrix exposed. In the case of the middle mechanical reinforcement layer containing perforated crosslinked acellular matrix, the said perforations are located in the perforations of crosslinked acellular matrix.

The crosslinking in the present invention refers to intramolecular or intermolecular covalent bonding between collagen molecules or between the collagen molecules and other components in the non-crosslinked acellular matrix by physical or chemical means, so as to block the targets of collagenases. Therefore, the resulted matrix will not be degraded or only partially degraded after implantation, and has similar or even better biomechanical properties than the synthetic mesh, thereby achieving the purpose of permanent reserve of part of the implanted undegradable fiber and stability of the repair area.

Effects of the Invention (1) The repair area of the present invention is stable in the long-term, without loss of laxity, bulging or shrinking. In the early stage of repair, the non-crosslinked acellular matrix of the upper and lower layers of the patch can induce rapid ingrowth of host cells and blood vessels. The non-degradable crosslinked component ensures that the lowest point of the mechanical properties of remodeled acellular matrix meets the needs of tissue repair and smoothly completes the transmission of tension. In the middle and late stage of repair, the non-crosslinked acellular matrix of upper and lower layers is remolded and combined with the crosslinked components implanted to maintain the tension-free repair of tissue defects for a long time, and finally the repair area achieves a long-term stable structure similar to "steel bar-concrete". Even under special circumstance, such as large-area abdominal defect repair, unsatisfied induced regeneration of non-crosslinked acellular matrix of upper and lower layers in central repair area, and the non-degradable crosslinked material can continue providing a certain mechanical tension to avoid the loss of elasticity and tissue bulging in the repair area.

(2) Good histocompatibility, no viscera erosion. The upper and lower layers of the repair material of the present invention contains non-crosslinked acellular matrix. The repair material has good histocompatibility, can directly contact organs such as the intestine, no viscera erosion. The middle mechanical reinforcement layers contain crosslinked acellular matrix, which is featured with biological viscoelasticity, without local high-tension points and other natural physical properties as same as non-crosslinked acellular matrix, fundamentally avoiding the incidence of viscera erosion.

(3) High integrity, low thickness, no dead spaces, good handling feel. Crosslinked acellular matrix and non-crosslinked acellular matrix can be firmly laminated through chemical bonds, with flat surface, uniform thickness and no delamination after cutting. The said repair material does not contain knitting nodes of synthetic fiber, which may thicken the material, low thickness, can be rolled and passed through trocar during minimal invasive surgery. The middle mechanical reinforcement layer can slow down the rehydration, improve the elasticity and flexibility of the material for the surgeon to use under laparoscopy. Large quantities of activated groups on the surface of molecules in the microstructure of acellular matrix are blocked during the process of manufacture of crosslinked acellular matrix, thus multilayered crosslinked acellular matrix cannot be stably laminated and chemical bonds cannot be formed under common technologies. For membrane-like acellular matrix whose thickness is low, lamination is needed to reinforce their mechanical strength. Thus, the present invention also discloses the composition methods for crosslinked and non-crosslinked membrane-like acellular matrix, such as small intestinal submucosa, urinary bladder matrix. The vacuum pressing and tying with suture can avoid delamination of the material, making it easy for the surgeon to cut the material into suitable shapes according to the wounds during the operation.

(4) Resistance to infection. In view that the biologic patch currently is mainly applied in contaminated or infected wound repair, the mechanical reinforcement layer introduced should avoid bacterial colonization at the early stage after implantation. Further, high-strength crosslinked collagen fibers are completely encapsulated in the acellular matrix layers, and the edge of which is 2 mm to 15 mm away from the edge of acellular matrix layers (the suture margin of surgery is generally 5 mm, and the distance of the present invention can ensure suturing to the mechanical reinforcement layer), which can ensure that the polymer fibers or crosslinked collagen fibers cannot directly contact the surrounding tissues in the early stage of implantation. The degradation of xenogeneic non-crosslinked acellular matrix is basically synchronous with the ingrowth of host tissue, thus effectively encapsulates crosslinked fibers at different time points, the fibers are difficult to directly contact the bacteria.

Besides, in the early stage of repair, the vascularization and infiltration of phagocytes of surface layers of non-crosslinked acellular is fast. Therefore, as a whole, resistance to infection of the "sandwich" structure should be similar to acellular matrix biologic patch. Further, the acellular matrix is mainly composed of type I and type III collagen fibers, with components such as laminin and glycosaminoglycan. The matrix is of high porosity and negatively charged, so that the positively charged anti-infective particles such as nano-silver particles, can be easily adhere to the matrix. Thus, anti-infective components in the adhered matrix can be continuously released to the surrounding extracellular matrix after implantation. Therefore, the repair material of "sandwich" structure can be easily developed into a material equipped with the ability of infective resistance with broad antibacterial spectrum, effectiveness and long-lasting time.

(5) Good abdominal wall compliance. Compared with synthetic material such as polypropylene, crosslinked acellular matrix processes better physical properties such as viscoelasticity, no large scars formation and improved patients' comfort and flexibility after surgery.

DETAILED DESCRIPTION OF THE PREFERRED EMBODIMENT

Figure 1:
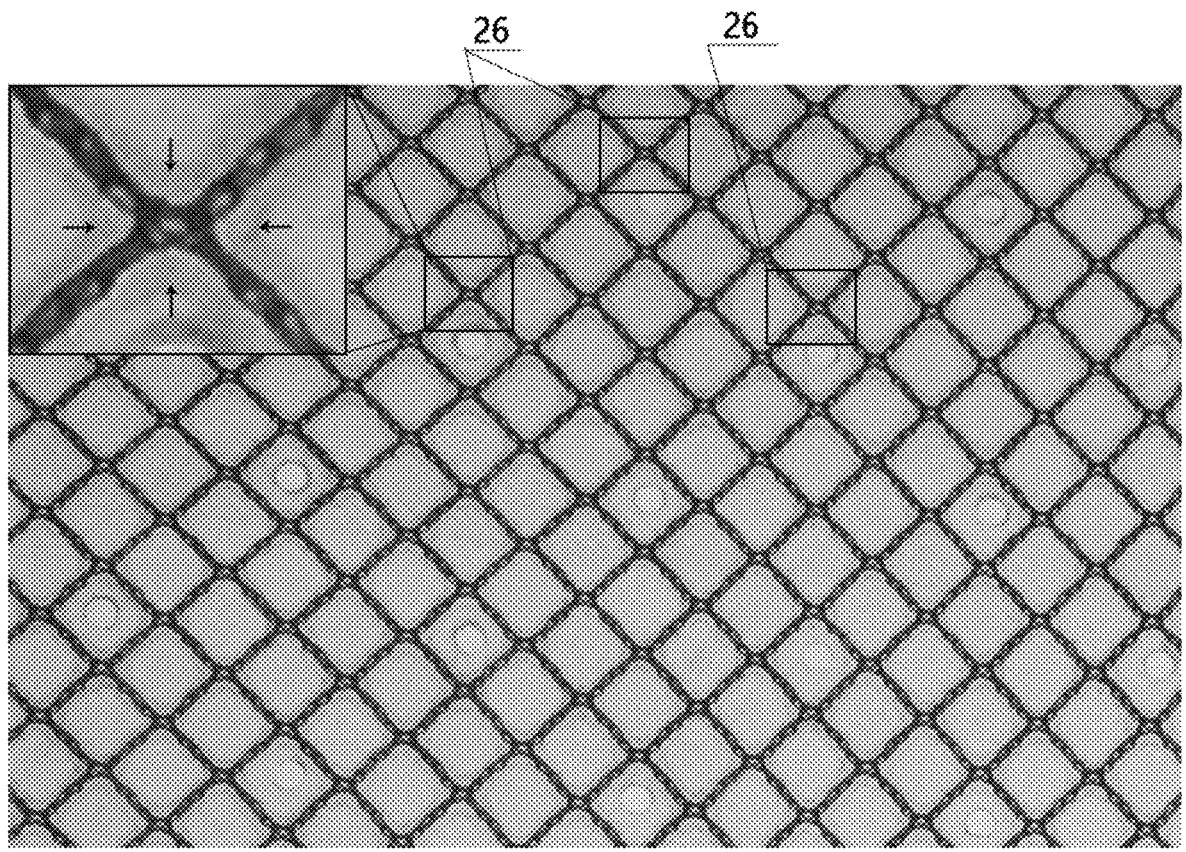
FIG. 1 is a schematic diagram of a prior art product.

The present invention provides a composite soft tissue repair material stable in repair area, which combines the advantages of crosslinked material and non-crosslinked material, including high histocompatibility, no viscera erosion, resistance to infection, mechanical stability of the repair area or the like, and thus has good application prospects.

Patent literature CN104822342A discloses a method and system for treating biological tissue, wherein the tissue prosthesis includes a support structure and an extracellular matrix (ECM) composition. The support structure includes synthetic material (e.g., Dacron, Orlon, Fortisaan, nylon, polypropylene, and expanded polytetrafluoroethylene), and natural material (processed sheep dermal collagen, crosslinked bovine pericardium, and human dura mater). ECM gel or emulsion or coating is deposited on the support structure to form a whole. The upper and lower layers of the present invention completely encapsulate the middle mechanical reinforcement layer, and are distinctly different from the support structure deposited with the ECM composition in the following aspects. (1) Composition technique: there is no technical difficulties to coated the support structure with the ECM composition, while the upper and lower layers of the present invention are both membrane-like materials, and their lamination with the middle mechanical reinforcement layer require that crosslinked and non-crosslinked acellular matrix to be placed by interlacing pattern or perforation of crosslinked acellular matrix, and vacuum pressing techniques or medical adhesive is required to form chemical bonds through physical methods. These lamination techniques are not well known or obvious to those skilled in the art. (2) In CN104822342A, ECM gel, emulsion or coating degrade fast (usually in 2 weeks post-implantation), which causes the burst release of active components and thus does not play the role of healing regulation. And fast degradation of ECM composition is inadequate to induce the tissue regeneration. The support structure will be exposed to viscera after degradation of the ECM coating, leading to viscera erosion.

There are some similar points in technical methods between the present invention and CN104822342A, while their objective and design are totally different. In CN104822342A, the key structure of the said prosthesis is the support structure, ECM composition is merely used to mitigate the inflammation response after the implantation of support structure. While the present invention is aimed at improving the stability of repair area after implantation of non-crosslinked acellular matrix in the long time, whose key structure is non-crosslinked acellular matrix. The crosslinked acellular matrix is merely used as supplemental mechanical security, improves the stability of repair area after implantation of non-crosslinked acellular matrix in the long time, no viscera erosion and no excess addition to the thickness of the material, and no formation of dead spaces which lead to infection. In common cases, non-crosslinked acellular matrix can realize satisfied endogenous tissue regeneration and stability in repair area, crosslinked acellular matrix is not the main mechanical support in the repair area.

The present invention will be further illustrated below in conjunction with specific embodiments. It should be understood that these embodiments are only used to illustrate the present invention and are not intended to limit the scope of the present invention. Further, it should be understood that various modifications and changes may be made to the present invention, and these equivalents also fall within the scope defined by the claims appended hereto.

FIG. 1 is a schematic diagram of a prior art product, wherein is dead spaces (26) are formed between polymer fibers and acellular matrix layers.

Figure 2:
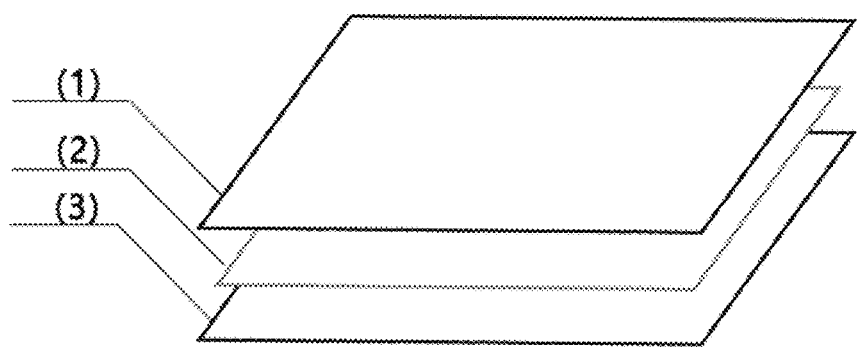
FIG. 2 is a schematic structural view of the present invention.

FIG. 2 is a schematic structural view of a composite soft tissue repair material of the present invention. The composite soft tissue repair material includes a middle mechanical reinforcement layer (2) and upper (1) and lower (3) layers.

Example 1

Non-crosslinked small intestinal submucosa (SIS) was prepared by Abraham method.

Figure 3:
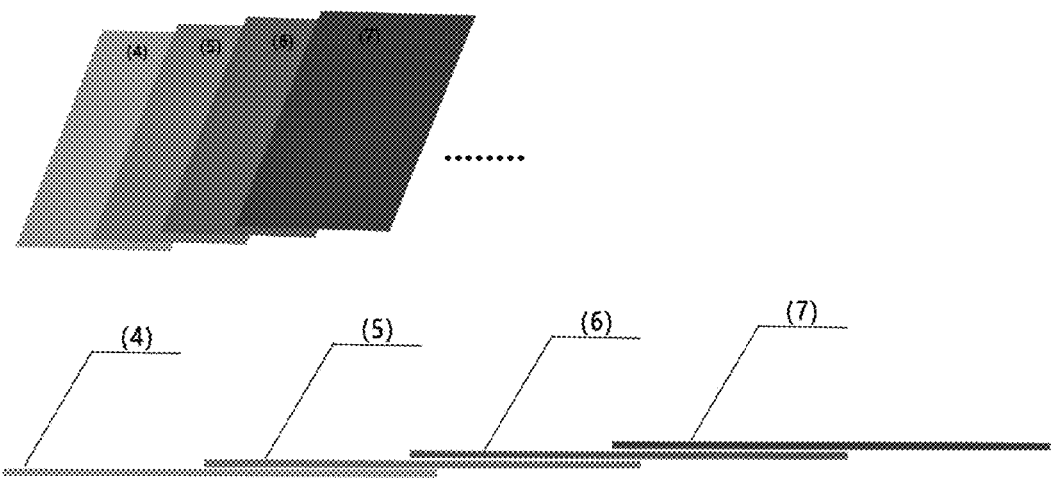
FIG. 3 is a schematic view showing a method for preparing the middle mechanical reinforcement layer of the present invention.

Non-crosslinked SIS sheets were spliced into a larger-area layer in an interlacing manner, namely upper or lower layers Crosslinked SIS was prepared by treating non-crosslinked SIS with 0.5% (w/v) genipin solution for 72 hours, crosslinking degree of which was 50% by ninhydrin method and weight was 38 g/m². The crosslinked SIS and the non-crosslinked SIS were composited to form a middle mechanical reinforcement layer by an interlacing method (FIG. 3), the method including the following steps:

Place a sterilized splint with rhombus hollows on a plate, lay a non-crosslinked SIS sheet (4) to allow an axial direction thereof be parallel along the edge of the splint, and place a sheet of non-crosslinked SIS (5) on the surface of crosslinked SIS sheet (4) so as to circumferentially overlap 50% of the crosslinked SIS sheet (4) and to maintain axial parallelism; place a sheet of crosslinked SIS (6) on the surface of the non-crosslinked SIS sheet (5) so as to circumferentially overlap 60% of the non-crosslinked SIS sheet (5), and the crosslinked SIS (4) to circumferentially overlap 10% of the crosslinked SIS sheet (6) and to maintain axial parallelism; and so on, place a non-crosslinked SIS sheet (7), so as to place a total of 4 crosslinked and non-crosslinked SIS sheets to form a first layer; Divide a non-crosslinked SIS sheet of appropriate length into two equal parts along the axial direction to supplement circumferential both sides of the first layer SIS, to form a middle mechanical reinforcement layer (2).

The middle mechanical reinforcement layer (2) and the upper and lower layers, i.e., non-crosslinked membrane-like acellular matrices, (1, 3) were placed to form a "sandwich" structure (as shown in FIG. 2), in which the mass ratio of the crosslinked acellular matrix in the middle mechanical reinforcement layer to the non-crosslinked acellular matrix in the layers was 10:1. The edge of the middle mechanical reinforcement layer was 5 mm away from the edge of the upper and lower layers. The layers were bonded by a medical chitosan adhesive.

Finally, sterilized splints with rhombus-like hollows was placed on upper and lower surfaces of the layers, and pressed under a vacuum pressure of −400 mmHg to obtain a material. The water residue in the material was extracted by using a water absorbing material. The material was perforated with voids spacing as 5 mm, diameter as 1 mm, which ensured that no crosslinked SIS was exposed in the perforations.

According to the standard GB/T528-2009 of China, the material was taken and cut into a dumbbell shape of 4 cm×1 cm. Two ends of the material were fixed by a mechanical tester and stretched at a speed of 10 mm/min. Tensile strength of the material was measured to be 53±5 N/cm.

An animal model of canine rectus abdominis anterior sheath and rectus abdominis muscle defect with local hypertension (a water bladder was added between the rectus abdominis posterior sheath and the repair material) was constructed, in which the defect area was 10×5 cm². The material was cut into a certain size for repairing the animal model. After surgery, the tension of the water bladder was increased to 40 mmHg by water injection month by month. For 24 months of observation, there was no abdominal wall bulging in the repair area. The tensile strength of the repair area was measured to be 32±5 N/cm.

Example 2

Figure 4:
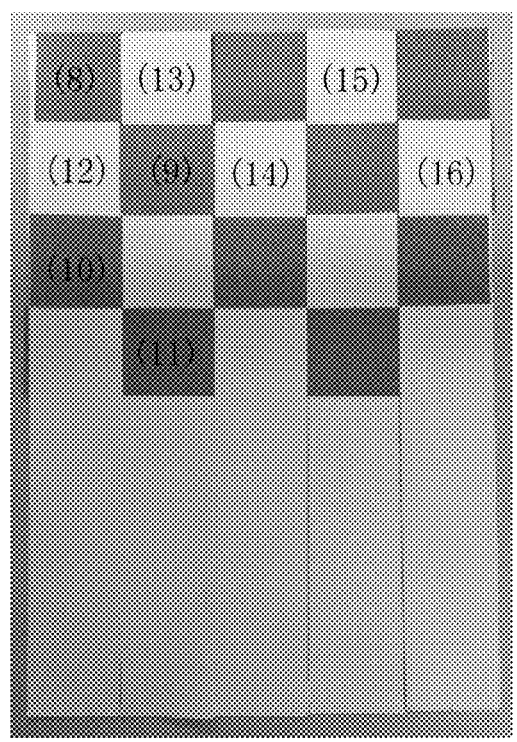
FIG. 4 is a schematic view showing a method for preparing the middle mechanical reinforcement layer of the present invention.

As shown in FIG. 4, crosslinked SIS and non-crosslinked SIS were prepared to be a middle mechanical reinforcement layer by a woven method, the method including the following steps:

Place a sterilized splint (100 mm×150 mm) with rhombus-like hollows on a plate, lay four crosslinked SIS sheets (8, 9, 10, 11) to a desired area and to allow an axial direction thereof be parallel to the horizontal direction of the splint, and maintaining axial parallelism of the SIS sheets, there being no gap or overlapping between two SIS sheets, so as to form a first SIS layer;

Fix the first SIS layer along the circumferential side, take a non-crosslinked SIS sheet (12) of appropriate length to make it axially perpendicular to the first SIS layer, forming a stable cross-stack between the first layer and the non-crosslinked SIS sheet (12) in an upper and lower alternating manner, after fix the non-crosslinked SIS sheet (12) along its circumferential side, place a non-crosslinked SIS sheet (13) in a manner of upper and lower alternating with the crosslinked SIS of the first layer and at the same time being close to the non-crosslinked SIS sheet (12), there being no gap or overlapping with non-crosslinked SIS sheet (12), and similarly, place non-crosslinked SIS sheets (13, 14, 15), so as to form a second SIS layer.

The above two layers formed one unit. The direction for laying subsequent units was shifted by 90° from the previous unit, and the unit was repeatedly placed to the required thickness. The middle mechanical reinforcement layer (2) and the upper and lower layers (non-crosslinked acellular matrices (1, 3)) were placed to form a "sandwich" structure (as shown in FIG. 2), in which the mass ratio of the crosslinked acellular matrix in the middle mechanical reinforcement layer to the non-crosslinked acellular matrix in the layers was 1:10. Another sterilized splint with rhombus-like hollows was placed on upper surface of the multi-layered SIS, and frozen at −80° C. for 2 h and then dried to obtain a composite material.

Example 3

Non-crosslinked urinary bladder matrix (UBM) and peritoneum were prepared by Abraham method. Non-crosslinked SIS was prepared as described in Example 1. The non-crosslinked SIS and the non-crosslinked UBM were composited to form upper and lower layers by an interlacing method as described in Example 1.

Crosslinked SIS was prepared as described in Example 1. Crosslinked porcine peritoneum was prepared by treating non-crosslinked peritoneum with 0.2% (w/v) glutaraldehyde solution for 6 hours, crosslinking degree of which was 80% by ninhydrin method. The crosslinked SIS, crosslinked peritoneum and non-crosslinked UBM were composited to form a middle mechanical reinforcement layer by a woven method as described in Example 2.

Example 4

Figure 5:
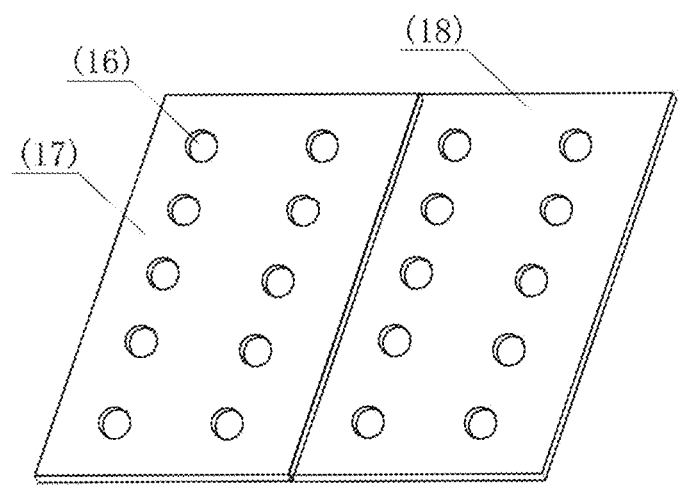
FIG. 5 is a schematic view showing a method for preparing the middle mechanical reinforcement layer of the present invention.

Non-crosslinked SIS and crosslinked SIS were prepared as described in Example 1. As shown in FIG. 5, circle-like penetrated voids (16) were made on crosslinked SIS (17), and several crosslinked SIS sheets (17, 18) were spliced into a whole, so as to prepare a mechanical reinforcement layer (2). The middle mechanical reinforcement layer (2) and the upper and lower non-crosslinked acellular matrix layers (1, 3) were placed to form a "sandwich" structure (as shown in FIG. 2), in which the mass ratio of the crosslinked acellular matrix in the middle mechanical reinforcement layer to the non-crosslinked acellular matrix in the layers was 1:20. The layers were tied with suture as a whole and lyophilized at −80° C., namely middle mechanical reinforcement layer.

Example 5

Figure 6:
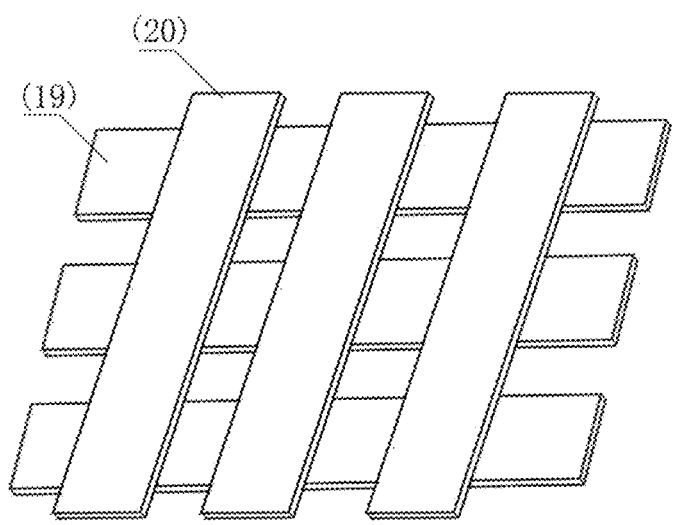
FIG. 6 is a schematic view showing a method for preparing the middle mechanical reinforcement layer of the present invention.

Crosslinked SIS sheets and non-crosslinked SIS sheets were prepared as described in Example 1. As shown in FIG. 6, the crosslinked SIS sheets were cut into strips of 2 cm×10 cm, and crosslinked SIS strips (19) were intermittently laid as a layer, on which another layer of crosslinked SIS strips (20) were laid above at a certain angle, these two layers were served as a middle mechanical reinforcement layer.

Example 6

Figure 7:
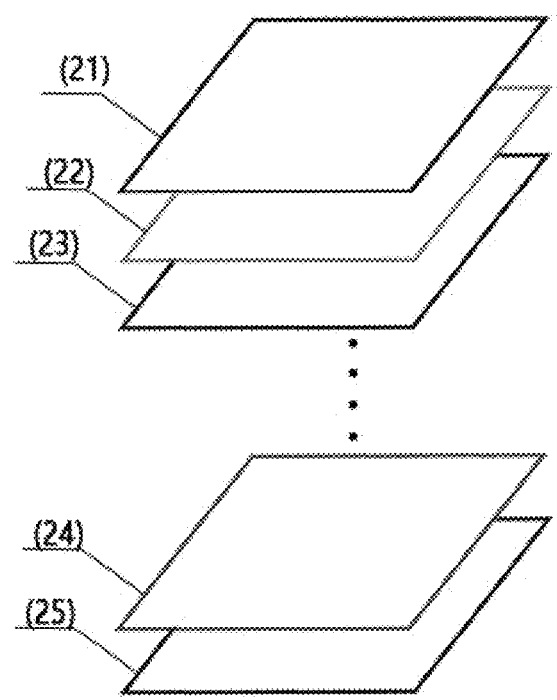
FIG. 7 is a schematic view showing a structure embodiment of the present invention.

Several mechanical reinforcement layers (22, 24) and non-crosslinked SIS layers (21, 23, 25) were prepared as described in Example 2. The layers were laid in the order of non-crosslinked SIS layer-mechanical reinforcement layer-non-crosslinked SIS layer (FIG. 7), placed under a pressure of −400 mmHg for 1 h, and freeze-dried into a whole, namely a composite soft tissue repair material stable in repair area.

The invention claimed is:

1. A composite soft tissue repair material stable in repair area, comprising:
    a middle mechanical reinforcement layer containing crosslinked acellular matrix;
    an upper layer containing a non-crosslinked acellular matrix; and
    a lower layer containing a non-crosslinked acellular matrix,
    wherein the upper layer and the lower layer completely encapsulate the middle mechanical reinforcement layer to form a sandwich structure,
    wherein chemical bonds are configured to be formed between the crosslinked acellular matrix and the non-crosslinked acellular matrix; and
    wherein the crosslinked acellular matrix is not degraded or only partially degraded after implantation.

2. The composite soft tissue repair material stable in repair area according to claim 1, where an edge of the middle mechanical reinforcement layer is 2 mm to 15 mm away from an edge of the upper layer and an edge of the lower layer, and
    wherein a tensile strength of the middle mechanical reinforcement layer is >8 N/cm.

3. The composite soft tissue repair material stable in repair area according to claim 1, where a mass ratio of the crosslinked acellular matrix in the middle mechanical reinforcement layer to the non-crosslinked acellular matrix in the upper layer and the lower layer is 1:20 to 1:0.1.

4. The composite soft tissue repair material stable in repair area according to claim 1, wherein the crosslinked acellular matrix is derived from submucosa of hollow organs, dermis, pericardium, peritoneum, pleura, basement membrane, or amniotic membrane of human or mammalian,
    wherein a number of layers of the crosslinked acellular matrix is 1 to 10, and
    wherein a crosslinking degree is 1% to 100%.

5. The composite soft tissue repair material stable in repair area according to claim 1, wherein the non-crosslinked acellular matrix is derived from submucosa of hollow organs, dermis, pericardium, peritoneum, pleura, basement membrane, or amniotic membrane of human or mammalian.

6. The composite soft tissue repair material stable in repair area according to claim 4, wherein to manufacture the middle mechanical reinforcement layer, the crosslinked acellular matrix may be laminated, selectively combined with non-crosslinked acellular matrix, into a whole layer through a woven pattern, or interlacing pattern, or perforated or strip-like crosslinked acellular matrix placed between the non-crosslinked acellular matrix, facilitating formation of chemical bonds between layers or sheets through physical methods.

7. The composite soft tissue repair material stable in repair area according to claim 1, wherein the middle mechanical reinforcement layer, the upper layer and the lower layer are laminated into a whole by one or more of medical adhesive, tying with suture, vacuum pressing and heat pressing.

8. The composite soft tissue repair material stable in repair area according to claim 1, wherein the material is further perforated penetrating the material,
wherein the perforations have a diameter of 1 mm to 50 mm,
wherein the spacing between perforations is 1 mm to 50 mm,
wherein no crosslinked acellular matrix exposed, and
wherein in the middle mechanical reinforcement layer containing perforated crosslinked acellular matrix, the perforations are located in the perforations of the crosslinked acellular matrix.

* * * * *